(12) United States Patent
Kusch et al.

(10) Patent No.: US 9,999,487 B2
(45) Date of Patent: Jun. 19, 2018

(54) METHOD FOR CREATING A VIRTUAL JAW IMAGE

(71) Applicant: SICAT GMBH & CO KG, Bonn (DE)

(72) Inventors: Jochen Kusch, Wachtberg (DE); Nils Hanssen, Bonn (DE)

(73) Assignee: SICAT GMBH & CO. KG, Bonn (DE)

( * ) Notice: Subject to any disclaimer, the term of this patent is extended or adjusted under 35 U.S.C. 154(b) by 85 days.

(21) Appl. No.: 14/403,194

(22) PCT Filed: May 27, 2013

(86) PCT No.: PCT/EP2013/060870
§ 371 (c)(1),
(2) Date: Nov. 24, 2014

(87) PCT Pub. No.: WO2013/175018
PCT Pub. Date: Nov. 28, 2013

(65) Prior Publication Data
US 2015/0132716 A1   May 14, 2015

(30) Foreign Application Priority Data

May 25, 2012 (DE) .......... 10 2012 104 543
Jun. 6, 2012 (DE) .......... 10 2012 104 912

(51) Int. Cl.
A61C 9/00   (2006.01)
A61C 19/045   (2006.01)
(Continued)

(52) U.S. Cl.
CPC .......... *A61C 19/045* (2013.01); *A61B 5/055* (2013.01); *A61B 6/14* (2013.01); *A61C 9/004* (2013.01);
(Continued)

(58) Field of Classification Search
CPC ....... A61C 19/04; A61C 19/045; A61C 19/05; A61C 9/004; A61C 9/0046; A61C 9/0053; A61B 6/00; A61B 6/14; A61B 6/145
See application file for complete search history.

(56) References Cited

U.S. PATENT DOCUMENTS 4,836,778 A   6/1989   Baumrind et al.
6,152,731 A   11/2000   Jordan et al.
(Continued)

FOREIGN PATENT DOCUMENTS

DE   10 2004 002 953 A1   8/2005
DE   10 2007 001 684 A1   8/2008
DE   10 2008 046 708 A1   10/2009

*Primary Examiner* — Tammie K Heller
(74) *Attorney, Agent, or Firm* — Norman B. Thot

(57) ABSTRACT

A method for generating a virtual jaw image includes performing a movement recording method to obtain a movement record which comprises producing at least one position data record over a defined time. A position data record describes a spatial position of a lower jaw to an upper jaw at a specific time. Surface sections of the upper and lower jaw are scanned at the defined time during the movement recording method to obtain a spatial relation of the surface sections during the defined time. Digital upper and lower jaw images are recorded. A position data record of a virtual position of the digital lower jaw image is assigned to the digital upper jaw image. A position data record is selected to obtain a selected position data record. The digital lower and upper jaw images are virtually aligned based on the selected position data record to produce the virtual jaw image.

12 Claims, 5 Drawing Sheets

(51) Int. Cl.
    *G06T 19/20* (2011.01)
    *A61B 5/055* (2006.01)
    *A61B 6/14* (2006.01)
    *G06T 7/33* (2017.01)

(52) U.S. Cl.
    CPC ............... *G06T 7/33* (2017.01); *G06T 19/20* (2013.01); *G06T 2210/41* (2013.01); *G06T 2219/2004* (2013.01)

(56) References Cited

U.S. PATENT DOCUMENTS

| | | | |
|---|---|---|---|
| 7,936,911 B2* | 5/2011 | Fang | A61C 19/045 382/128 |
| 2002/0048741 A1 | 4/2002 | Jordan et al. | |
| 2003/0204150 A1 | 10/2003 | Brunner | |
| 2010/0124367 A1 | 5/2010 | Cizek | |
| 2013/0130195 A1 | 5/2013 | Evenson | |

\* cited by examiner

METHOD FOR CREATING A VIRTUAL JAW IMAGE

CROSS REFERENCE TO PRIOR APPLICATIONS

This application is a U.S. National Phase application under 35 U.S.C. § 371 of International Application No. PCT/EP2013/060870, filed on May 27, 2013 and which claims benefit to German Patent Application No. 10 2012 104 543.7, filed on May 25, 2012, and to German Patent Application No. 10 2012 104 912.2, filed on Jun. 6, 2012. The International Application was published in German on Nov. 28, 2013 as WO 2013/175018 A1 under PCT Article 21(2).

FIELD

The present invention relates to a method for generating a virtual jaw image.

BACKGROUND

An overall system of bones, teeth, temporomandibular joints, and muscles is considered in functional dentistry. Complicated movement sequences of the whole system, which are individual to the patient, are increasingly recorded by means of electronic methods that are able to register the position of the lower jaw in relation to the upper jaw at different times in six degrees of freedom (three rotations, three translations). Such movement records may be available as condylography data.

DE 10 2004 002 953 A1 describes a method in which the relative motions of the jaws are measured on the basis of two ultrasonic transducers and sensors rigidly connected to the upper and lower jaw. By means of a prepared representation of the thus obtained condylography data, the dentist is able, for example, to also depict the movement trajectory of an imagined hinge axis of the temporomandibular joints during masticating. This prepared representation of the movement trajectory of an imagined hinge axis corresponds to the measurement that is recorded, usually by direct mechanical means, in relatively old measurement systems (so-called axiography systems). Such axiography systems do not measure the full six degrees of freedom of the lower jaw position, but only an angle/path combination from which the spatial position of the lower jaw in relation to the upper jaw usually cannot be uniquely established. The axis tracing is nevertheless often displayed, even in the case of condylography systems with the full six degrees of freedom, because medical practitioners are trained to diagnose pathologies on the basis of this tracing data.

Even if many pathologies in the joint and muscular anatomy can be diagnosed by condylographies or axiographies, the diagnosis often needs to be differentiated by means of imaging methods which depict hidden anatomy in a geometrically correct manner. Examples for such imaging methods include cone-beam computed tomography (CBCT), magnetic resonance imaging (MRI), and computed tomography (CT). Making tomographic images is often also essential for the therapy planning that follows the diagnosis. This is particularly the case if changes have to be undertaken on the bone, e.g., during an orthodontic treatment or in a surgical intervention.

The positional relationships between the jaws were until now typically not even scanned during a tomographic scan. The patient is instead scanned with an undefined jaw position by virtue of said patient being fixed with a generic bite block or by virtue of his head resting on a chin support. If a bite block is used, the teeth are slightly opened; in the case of the chin support, the teeth are in occlusion or maximum intercuspation.

Some recording protocols, in particular, in magnetic resonance imaging, prescribe a specific jaw opening for being able to diagnose the position of the disk in the temporomandibular joint. This jaw opening is typically established by a cylinder with a diameter of a few centimeters which the patient holds between his teeth during the recording. Opening the patient's mouth by means of a cylinder, however, only permits very approximate influencing of the relation between upper and lower jaw. This can moreover only set relations in which the temporomandibular joints are in a central position. Transverse and lever forces cannot be exerted by a cylinder.

This is aggravated by the fact that patients are often referred from an orthodontist or dentist to a specialist in recording tomographic volume data who, however, generally does not have specialist knowledge in the field of dentistry. Such specialists are generally unable to monitor or set the precise position of the jaw.

When diagnosing and treating problems of the temporomandibular joint, care should be taken, in principle in all recordings of the jaws, that, where possible, no unnatural or undesired forces act on the jaws. By way of example, when performing a tomographic method in the intercuspation position (ICP), there may be an—albeit small—deformation of the jaws, or the temporomandibular joint may assume an unnatural position due to the muscle power. This would naturally significantly reduce the quality of the digital images. Tomographic recordings, and other recordings, which were recorded in the ICP are, as a matter of principle, furthermore relatively unsuitable since the image data in the boundary regions between upper and lower jaw can often only be assigned poorly to the respective jaw in an automated manner.

An aspect of the present invention is to make further use of the diagnostic options emerging from condylography.

In an embodiment, the present invention provides a method for generating a virtual jaw image depicting a digital lower jaw image in relation to a digital upper jaw image in different positions which includes performing a movement recording method to obtain a movement record. The movement recording method comprises producing at least one position data record over a defined time. Each of the at least one position data record describes a spatial position of a lower jaw in relation to an upper jaw at a specific time. Surface sections of the upper jaw and of the lower jaw are scanned at the defined time during the movement recording method so as to obtain a spatial relation of the surface sections during the defined time. Digital upper jaw images and digital lower jaw images are recorded. At least one of the at least one position data record of a virtual position of the digital lower jaw image is assigned in relation to the digital upper jaw image. One of the at least one position data record is selected so as to obtain a selected position data record. The digital lower jaw image is virtually aligned in relation to the digital upper jaw image in accordance with the selected position data record so as to produce the virtual jaw image. The virtually aligning corresponds to a real position of the lower jaw in relation to the upper jaw in accordance with the selected position data record.

BRIEF DESCRIPTION OF THE DRAWINGS

The present invention is described in greater detail below on the basis of embodiments and of the drawings in which.

DETAILED DESCRIPTION

Figure 1:
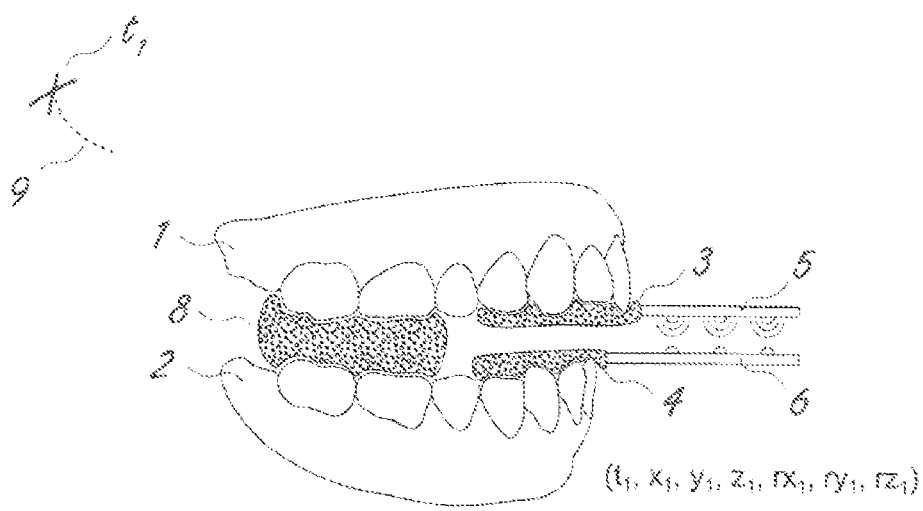
FIG. 1 shows a condylography of upper and lower jaw and the axis tracing calculated therefrom.

The core of the present invention, in particular, lies in the fact that digital images of the upper jaw and of the lower jaw generated at any time and therefore with a jaw position not defined in any more detail, for example, in CBCT scans or the like, can now, on the basis of the movement record, be brought into any predeterminable position, which moreover corresponds to a real position of the lower jaw in relation to the upper jaw, in relation to one another. In the process, for example, a pathology can be deduced on the basis of the movement record at a specific time in a first diagnostic step. Details in respect of this pathology, however, can often only be gathered to a restricted extent from the movement record alone. Using the present invention, it is now possible, for example, to show the temporomandibular joint in the position of lower jaw and upper jaw to be evaluated, as a result of which further findings and diagnoses can be produced, without an additional further imaging method at the desired jaw position necessarily being required in this case. It is likewise possible also to select other times, specifically, a time just before the determined time or a time just after the determined relevant time. The corresponding position of the jaws in relation to one another can be visualized by simple virtual alignment of the digital lower jaw image in relation to the digital upper jaw image. This consequently creates diagnostic possibilities which were previously unknown and, at best, could be replaced by moving tomography methods which, however, are much more complicated and would expose the patients to significantly more ionizing radiation. The user can now set the desired time of the movement record at the computer and can then obtain a graphic representation of the jaw position.

As movement recording methods use is, in particular, made of the condylography method which, in the subsequent description, is also mentioned as a representative for other movement recording methods. The result of a movement recording method is the movement record, wherein, in the following text, reference is made to the condylogram or the condylography data as a representative for the results of other methods.

The employed digital volumetric images of the jaws in this case originate from the person themselves on whom the condylography method was performed. The upper jaw image and the lower jaw image can, for example, be respectively generated here in any jaw position by means of an imaging method. The position of the lower jaw in relation to the upper jaw during the imaging method can therefore in particular be one which deviates from the virtual alignment of the virtual jaw image to be generated. In this respect, it is therefore no longer mandatory for the digital images of the upper jaw and of the lower jaw to be recorded in precisely such a position in which the condylogram has indicated a possible pathology. What suffices is to rather initially record the real jaw in "any" position in order then to at least virtually reproduce any jaw position in the simulation referred to above. A person skilled in the art is able, by means of the method according to the present invention, to fuse condylography data and volumetric, in particular tomographic, recordings.

In order to select the position data record, a time in the profile of the movement record is selected and the associated position data record is then identified and hence selected on the basis of the selected time. The position data records are here recorded over a certain period of time, wherein each position data record is at least indirectly assigned to a time in the masticating motion. The time need not necessarily be here reflected in a temporal unit but can, for example, also be assigned to the mouth opening angle during opening and closing.

The position data record can here represent a location of at least one or more points connected in a fixed manner to the lower jaw in relation to a reference system which is securely connected to the upper jaw, respectively, at the time of the recording during the condylography method. How the lower jaw itself is then disposed in relation to the upper jaw in absolute terms cannot necessarily be gathered directly from the position data records. The position of the lower jaw in relation to the upper jaw is, however, either already known or can still be established at at least one time in the condylogram; to this end, in particular, a bite registration can establish the absolute alignment of the upper jaw in relation to the lower jaw in respect of at least one single position data record. With this, it is then also possible to establish the corresponding jaw positions for the remaining position data records. By way of example, the alignment can be brought away so that a surface scan of the bite registration is performed. The surface data of the upper jaw and lower jaw are of course already known from the respective digital upper and lower jaw images. "Matching" is then undertaken. This means that the position data record for the defined time is called, and then the surface data of the bite registration in relation to the digital lower jaw image and then the bite registration in relation to the digital upper jaw image are aligned virtually. Using this, the alignment between the digital upper jaw image and the digital lower jaw image is then established. The further alignments of the two jaw images at other times can then be played back by "forwarding" through the condylogram.

Tomographic data (digital jaw images) of the jaw and of the lower jaw are consequently acquired or generated in the method according to the present invention. When generating the data, the relative position of these two jaws in relation to one another is irrelevant since all that matters are the data of the jaws per se. Separately from this, a condylography method (movement recording method) known per se is, for example, performed, by means of which the relative movements of the jaws are established. During the condylography method, a bite registration is generated at least once, or a relative position between upper jaw and lower jaw is determined by other means (scanning of the surface sections at the defined time). Using this, the tomographic data of the two jaws in relation to one another are then synchronized spatially. A data value is consequently obtained from the condylography method, for which the correct spatial alignment of the two jaw images with respect to one another is known. If the relative alignment of the two jaw images on a corresponding different data record of the condylography method is now modified, what is obtained is the relative alignment of the two digital jaw images, which correspond precisely to the real alignment of the real jaws as this other data record was generated on the real test person. By way of example, this other data record can now be a data record, in respect of which the condylography indicates a pathology. It is now possible to look at the digital jaw images of this suspected pathological position and evaluate these accordingly.

In an embodiment of the present invention, a surface image, for example, a 3D photography, of the real upper jaw and of the real lower jaw can, for example, be made during the scanning, wherein the time of this 3D photography corresponds to a time of the movement record. For example, the 3D photography can then be linked by a method as is described in DE 10 2007 001 684 A1 to the digital upper and lower jaw images.

Although the alignment could already be performed by virtue of the digital upper jaw image and the lower jaw image already being recorded in intercuspation, the unique assignment of the upper and lower jaw imprints on the basis of the engaging dental cusps cannot always be uniquely determined. The method according to the present invention, however, also offers the advantage that, as a result of the option of using upper jaw images and lower jaw images which were recorded in "any" jaw position, it is possible to provide that these jaw images do not have tension or deformations which could emerge from biting together.

The specific time also means a specific position in the graph of the axiogram or in the position data records of the condylogram.

The present invention furthermore relates to a method for producing a scan splint, wherein a method for generating a simulation of the type set forth above is carried out. A scan splint is here furthermore produced on the basis of the virtual jaw image, wherein the scan splint comprises at least one defined upper jaw abutment surface and one defined lower jaw abutment surface. The upper jaw abutment surface and the lower jaw abutment surface are aligned with respect to one another so that the real lower jaw assumes the spatial position in relation to the real upper jaw in accordance with the selected position data record when the upper jaw abutment surface abuts the upper jaw and the lower jaw abutment surface abuts the lower jaw. Upper jaw and lower jaw here respectively mean the real upper and real lower jaws. Within the scope of the present invention, to be in abutment with a jaw, however, also means an at least indirect abutment with the jaw, wherein the direct abutment is to be understood to mean with an object, in particular, a tooth, held stationary in relation to the jaw. The abutment to a tooth here also corresponds to the abutment with the associated jaw. The jaw abutment surfaces can here in particular be those surfaces which, at least in sections, are formed inversely in relation to the tooth surfaces. The jaw abutment surfaces can then be connected to form a common object, namely the scan splint. The scan splint then comprises the geometric surface sections of the two jaws which are aligned with respect to one another precisely like the real surface regions of the jaws in the selected jaw position. By way of example, such a splint can then be formed by a milling cutter, a stereolithography method or a 3D print. The scan splint can therefore be used at any time to reproduce, in reality, real jaw positions which were diagnosed as conspicuous on the basis of the condylogram.

In a further, subsequent method step, it is also possible to produce digital volume data, wherein the scan splint is brought into abutment with the lower jaw and the upper jaw and, subsequently, the upper jaw and the lower jaw with respectively applied scan splint are brought to a tomographic image recording method. It is then in particular possible to by means of a tomographic image recording method to produce a new image, wherein, during the image recording, the real lower jaw is held in a position in relation to the real upper jaw in accordance with the selected position data record. During the recording method, the scan splint is applied to the patient to provide that the jaws are in the desired position during the recording method. It was thus initially determined during the preceding method steps which jaw position is problematic and requires a further examination, and how it is possible to reproduce this real jaw position. The scan splint was then manufactured, with the aid of which the real jaw can now always be brought into the problematic position, namely, in particular, for the purpose of performing a scan, in particular a CBCT, specifically in the problematic position. The advantage now consists of the scan splint bringing the jaws into a natural position in relation to one another, since this position corresponds to a data record from the condylography method.

In relation to the virtual jaw image already presented above, it is possible, by means of the further image, to visualize (also or only) non-rigid components of the jaw or adjoining tissue regions, in particular, flexible parts such as cartilage, muscles etc. in precisely the relevant jaw position. It is possible as a result to make further statements about possible pathology, which statements themselves cannot be gathered or can only be gathered to an insufficient extent, from the virtual jaw image which is based on the condylography data. The advantage then, in particular, lies in the fact that this new image can completely depict the situation in the situations diagnosed as conspicuous in the condylogram. As a result of the forced relationship of the teeth in relation to one another during the tomographic recording method, it is possible to diagnose the temporomandibular joint with the disk and the involved soft tissue particularly well on the basis of the volumetric tomographic recording.

In order to be able to check a suspected diagnosis from a condylography in an imaging system in a targeted manner, the present method can now be used to set the positional relation of the jaws to one another, i.e., a specific jaw position, in a targeted manner. If something conspicuous was determined at a specific time in the masticating process in the condylography data, precisely this positional relation between upper and lower jaw which was given at this time of the jaw movement will also prevail in the image of the upper jaw and of the lower jaw now generated. A very high significance can thus be provided using a combination of axiography with an imaging method. The positional relations just before or just after this specific time are also of great interest for differential diagnostics using imaging methods.

The above-described fusing of movement and volume data now also enables the preparation of the condylography data on the basis of anatomical conditions. By way of example, the representation of an axis tracing, known from axiography, can now also be parameterized on the basis of the anatomical conditions. Instead of deriving the axis and the movement trace thereof purely from the kinematics of the movement record, it is possible for, for example, the shape of the jaw condyles (only visible in tomography) and the gradient of the socket to influence the selection of the axis and hence also the axis tracing.

It is now possible to depict the corresponding movement in the volumetric tomography data (for example, by playing back an animation of the moved volumetric tomography data) for each time interval of the movement record.

A further advantage of fusing movement and tomography data is that the movement trajectory of each point of the lower jaw can now be reconstructed. As a result of this information, representations which prepare the movement trajectory of individual points for the user are possible. There can in particular be a representation where it is not even necessary to play back an animation, but the trajectory of points in time is once again displayed as a tracing in space. The selection and/or preferred representation of anatomical points which have specific kinematic properties are therefore also possible. By way of example, points can be highlighted in the lower jaw, e.g., as a selected element, which (i) move particularly quickly, (ii) move uniformly, (iii) are accelerated particularly strongly, and (iv) pass over a particularly large or particularly small path or do not move at all. It is also possible to establish points on the bone and/or on the teeth which, on the left-hand and right-hand side of the jaw, have symmetric or asymmetric properties in relation to the kinematic variables described above ("kinematic/functional symmetry" as opposed to morphological symmetry).

Conversely, tomography can now be used to select regions of interest in the condylography (which of course usually consists of a plurality of recording series). By way of example, the treating practitioner can click onto a tooth or a point as the element to be selected on the tooth, jaw bone or temporomandibular joint, and have shown to him the time intervals and tracings of the animation in which the selected point exceeds or drops below one of the kinematic variables listed above. By way of example, the condylography recording for a point on a lower incisor in which this incisor point is accelerated most strongly can be selected or the condylography recording in which this tooth point passes over the longest path can be selected.

By virtue of the above-described fusing of digital images and movement data, the movement data can, according to the present invention, also be used in all visualizations which are derived from volumetric tomography data. By way of example, projection recordings can be calculated from the tomographic volume data which corresponds to cephalometric x-ray recordings in different jaw positions without having to expose the patients to more ionizing radiation. According to the present invention, such x-ray recordings can also, for the first time, be calculated and depicted as an animation individual to the patient. The irradiation direction of such calculated x-ray recordings can now furthermore be selected depending on the recorded movement record. By way of example, an irradiation direction which respectively extends along the hinge axis direction of the temporomandibular joints, calculated from the movement data, is particularly advantageous; as a result, the irradiation direction can also change for each time of the movement record.

Other simulated recordings can now also profit from the movement record. By way of example, it is now also possible to calculate a panoramic recording or an animation of panoramic recordings from the volumetric volume data, which is parameterized on the basis of the movement record. By way of example, the panoramic recording can be calculated and displayed so that it is as symmetrical as possible in relation to movements measured on the left-hand and right-hand side of the jaw. It is also possible for dental film recordings and dental film animations to be calculated from the tomographic data, which, for example, show the teeth of the upper and lower jaw when (i) they have no contact, (ii) they have first contact, or (iii) they are in maximum intercuspation. It is once again furthermore possible to display movement tracings of any point on the teeth and jaws in the projection recordings calculated thus, for example, by virtue of passing over a point in a projection recording by means of an input device, in particular using a mouse. The movement track of the element selected can be statistically evaluated during a movement sequence based on the movement record.

The present invention furthermore relates to a scan splint which is manufactured by a method of the type set forth above.

The present invention will be explained in more detail below on the basis of the figures.

Figure 2:
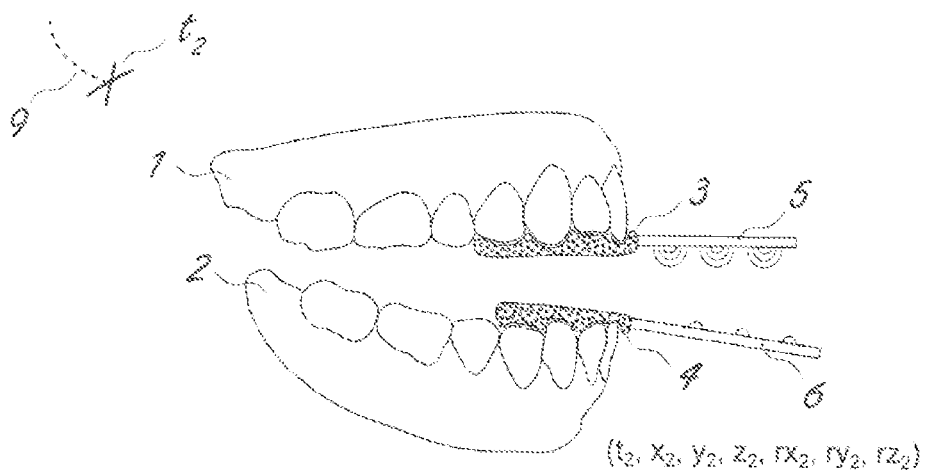
FIG. 2 shows a condylography of upper and lower jaw and the axis tracing calculated therefrom.

FIGS. 1 and 2 depict the condylography on the basis of two different jaw relations at the times $t_1$ and $t_2$. Here, the upper jaw 1 is provided with an actuator element 5 which is rigidly connected by means of an upper denture piece 3. The lower jaw 2 is provided with a sensor element 6 which is rigidly connected by means of a lower denture piece 4. The actuator element and sensor element can also be fastened to the respective other jaw. As a result of the jaw movements being rigidly transferred onto the actuator and sensor elements and as a result of knowing the actuator and sensor element geometry, it is possible to deduce the relative movements of upper and lower jaw on the basis of the signals measured in the sensor element 6. A 6-tuple can therefore be measured at each time $t_j$ during the condylography, which 6-tuple contains the translation and rotation of each point in space of this rigid transformation. From these data, it is possible to calculate an imagined axis tracing 9 for a movement or for a movement section. By means of a bite registration 8, the jaw relation at the time $t_1$ can be put into a definite geometric relation and, thereby, the latter can be calculated at any other time $t_j$ on the basis of the condylography. In some systems and recording protocols, the upper denture piece 3 and the lower denture piece 4 are also embodied in such a way that they do not cover the occlusal surfaces of the teeth. In such a case, the movement of the teeth can be recorded as far as the final bite position (intercuspation).

Figure 3:
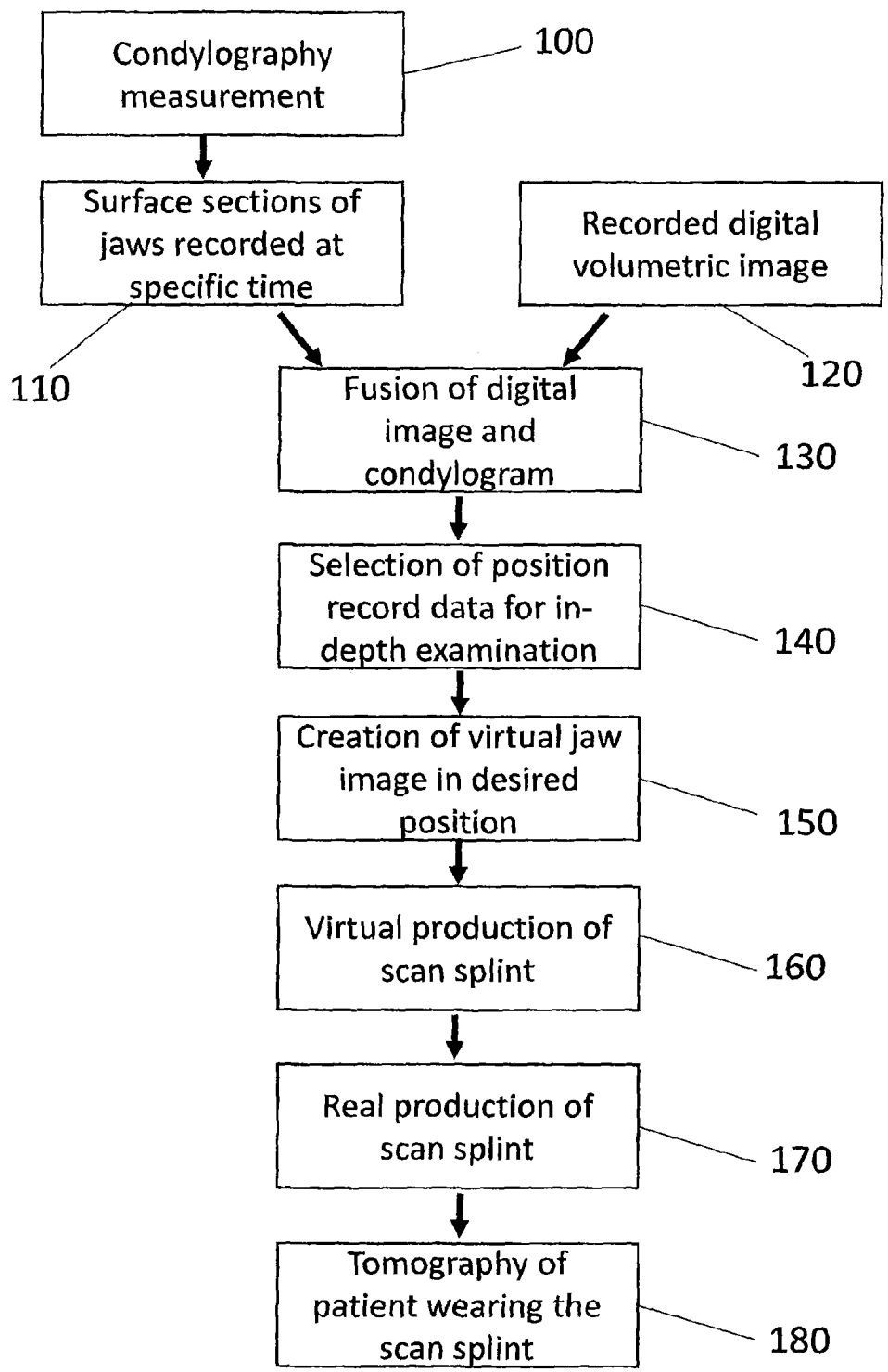
FIG. 3 shows a flowchart in a block diagram.

FIG. 3 schematically explains the method according to the present invention using a block diagram. In a first step 100, a condylography method is performed, which is already known from the prior art and was explained in FIGS. 1 and 2 on its merits. A multiplicity of position data records are thus recorded for further use. In step 110, surface sections of the real upper jaw and of the real lower jaw are now recorded at a specific time in the condylography method, wherein the relative alignment between upper jaw and lower jaw in relation to one another is also taken into account in this scanning method. By way of example, this can be brought about by the bite registration 8, as shown in FIG. 1. The test person here bites the bite registration, for example, a soft wax material, for example, at the time $t_1$ in FIGS. 1 and 2, at which the teeth are, for example, almost closed. The bite registration then scans surface regions of the upper jaw and of the lower jaw in a real situation during the masticating process. In the block diagram according to FIG. 3, this process is documented by step 110. In this process, what is, however, also recorded is that this scanning occurs precisely at this time $t_1$, and so the imprint which remains on the bite registration 8 can be brought into direct correlation with the condylogram according to FIGS. 1 and 2. The bite registration 8 is then scanned and digitized.

In step 130, the condylogram is now fused with arbitrary digital volumetric images of the upper jaw and of the lower jaw. To this end, digital upper jaw images and digital lower jaw images were previously recorded in step 120, for example by means of a tomographic method. Purely from the spatial separation between the branch with the functions 100 and 110 and the branch with the function 120, it is already possible to deduce that recording the condylogram is completely independent of recording the digital volumetric upper and lower jaw images according to method step 120. The advantage consists of the fact that use can be made of digital volumetric upper jaw and lower jaw images which were made at some time. For the purposes of fusing the digital volumetric upper and lower jaw images, for example the tomography recordings, with the condylography data, the scanned surface regions of the bite registration 8, or of another scanning method, are compared to the surface data of the digital volumetric upper and lower jaw images. The digital volumetric upper and lower jaw images are here aligned with respect to one another so that these are in correspondence with the surface sections of the scanned bite registration. So that this can take place, a so-called segmentation can, if need be, be performed in the volumetric data, which segmentation defines which parts of the volumetric data correspond to the movable lower jaw and which do not. There is thus then an alignment of the digital volumetric upper jaw image and of the digital volumetric lower jaw image in relation to one another such that the position of the two images is exactly aligned with respect to one another as the real upper jaw and lower jaw were at the time $t_1$, as the bite registration was produced during the condylography method.

In step 140, a position data record is now selected for a more in-depth examination, for example, the position data record for the time $t_2$ near the opened jaw position. By displacing the digital volumetric lower jaw image in relation to the digital volumetric upper jaw image in step 150, the virtual jaw image is thus created in which the digital volumetric lower jaw image is depicted in a desired position in relation to the digital volumetric upper jaw image. This position corresponds to a real position, which was in fact also assumed by the real jaw during the condylography method.

Further examinations or measures can be taken on this aligned virtual jaw image. By way of example, the arrangement of joint elements in the temporomandibular joint can be precisely analyzed in this virtual jaw image and can be examined in respect of possible pathologies. For this examination, use can substantially be made of only the image information which is available by the digital volumetric upper and lower jaw images. In the case of tomography, these are the bony structures since these move following a rigid transformation. The position of the soft tissue involved in the movement cannot, however, always be acquired directly. If this examination should thus be insufficient, further steps can be initiated with the aid of this virtual jaw image.

This virtual jaw image can in particular be used for manufacturing a scan splint. Such a scan splint is a real existing splint, which can be placed between the real upper jaw and lower jaw and thus brings the real upper jaw into a defined alignment with respect to the real lower jaw or holds said real upper jaw in this defined alignment. To this end, the surface data can be extracted from the virtual jaw image and a surface for the scan splint can hence initially be generated virtually. Abutment surfaces for the teeth or other parts of the jaw are therefore generated in this virtual scan splint, wherein the desired relative alignment of the jaws with respect to one another of course remains accounted for. By means of a milling, rapid prototype or similar method for manufacturing real objects, this virtually manufactured scan splint can then also be implemented in reality. If the patient inserts this scan splint, the patient then in reality assumes the jaw position which corresponds to the jaw position in the virtual jaw image. Further examinations can now be performed on the basis of this real jaw position. A further imaging method can in particular be performed for manufacturing a new volumetric image, for example, a tomography method in which the joints, or other parts of the jaw to be examined, of the patient are recorded in this concrete position to be examined. In such a method, it is then also (or only) possible to record elements, for example, muscles, cartilage and tendons, which are flexible and precisely cannot be reproduced exactly by the preceding simulation. The virtual production of the scan splint is represented by step 160. The real production of the real scan splint is visualized in step 170. In step 180, the tomography method, in which the patient wears the scan splint, is then performed.

Figure 4:
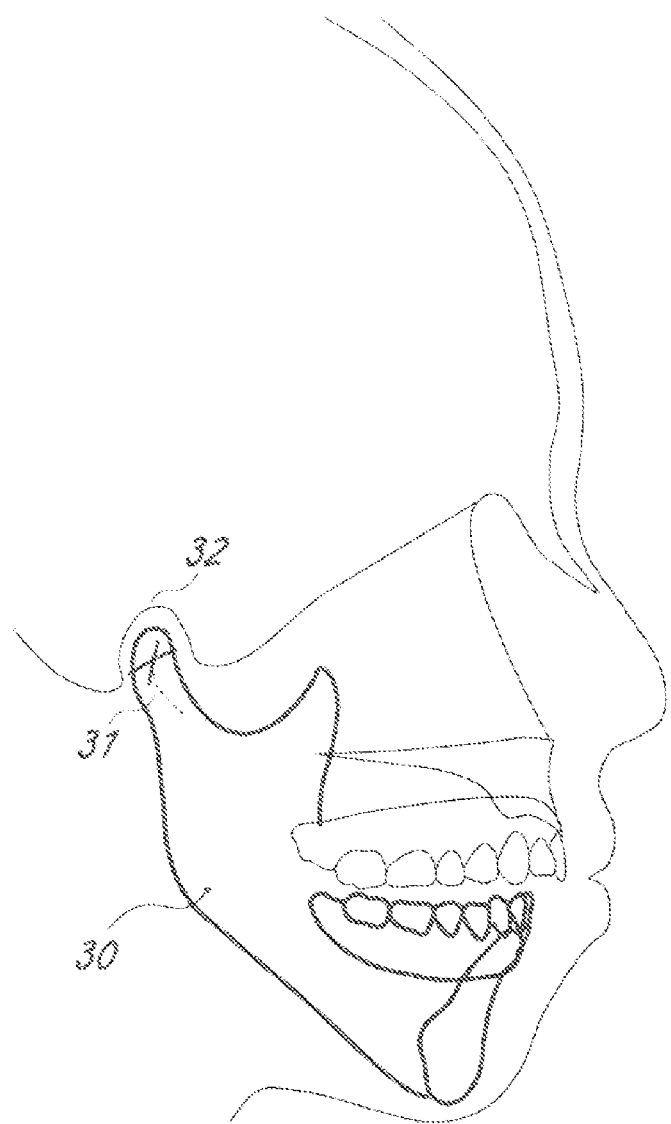
FIG. 4 shows a fusing of upper and lower jaw movements and tomography data.

FIG. 4 shows the fusing of condylography data and the digital volumetric upper and lower jaw images at the time $t_1$. The thick lines combine the bone anatomy of the lower jaw 30 which move together as a rigid object during a masticating process. As a result of this rigid connection, the movements of the condylography measured at the teeth can also be transferred to the bony regions of the anatomy visible in the tomography. It is now also possible to select a new axis point with tracing 31, which takes this anatomy into account, for display purposes. The selection of this "anatomical" axis point can in particular also be selected dependent on the geometry of the joint fossa 32 or on other anatomical structures.

Figure 5:
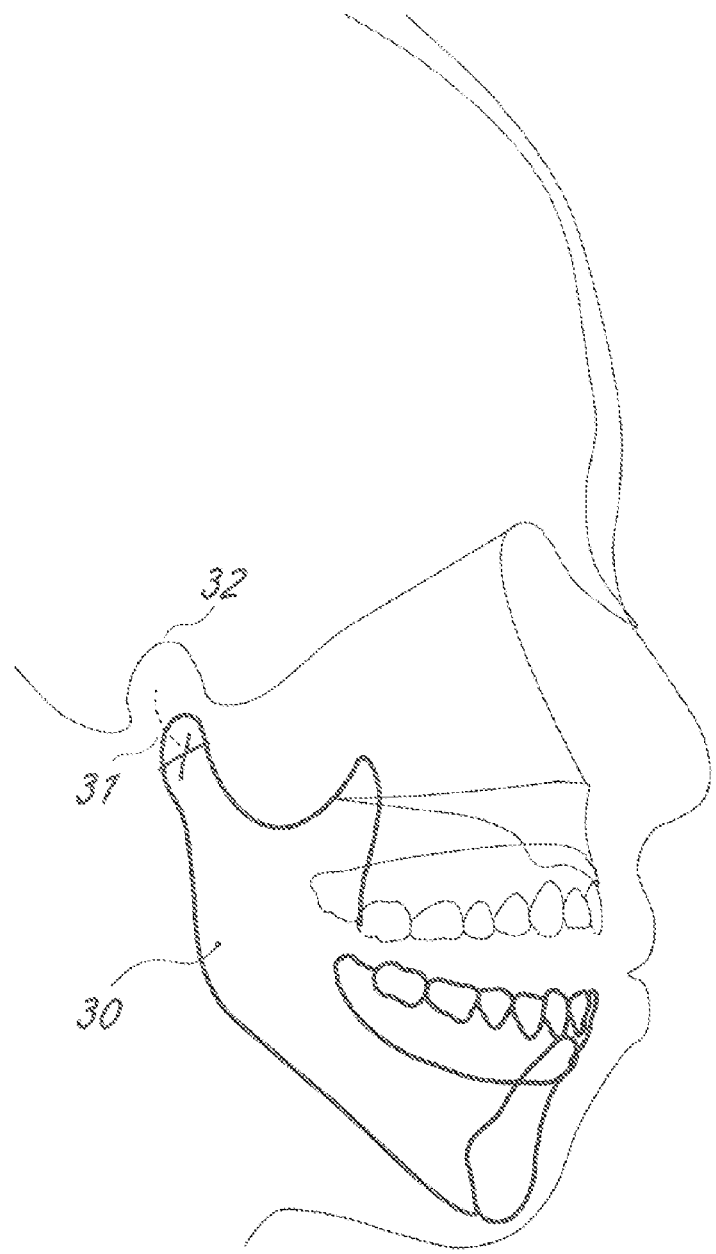
FIG. 5 shows a fusing of upper and lower jaw movements and tomography data.

FIG. 5 shows the situation at the time $t_2$. As a result of the rigid connection of teeth and bones in the lower jaw, the movement now measured by the condylography can also be transferred onto the bone anatomy of the lower jaw 30 depicted in the tomography. As a result, the bone anatomy of the lower jaw 30 of the slice image generated at the time $t_1$ can be displayed in such a way as if the slice image was recorded in the jaw relation of the time $t_2$.

Figure 6:
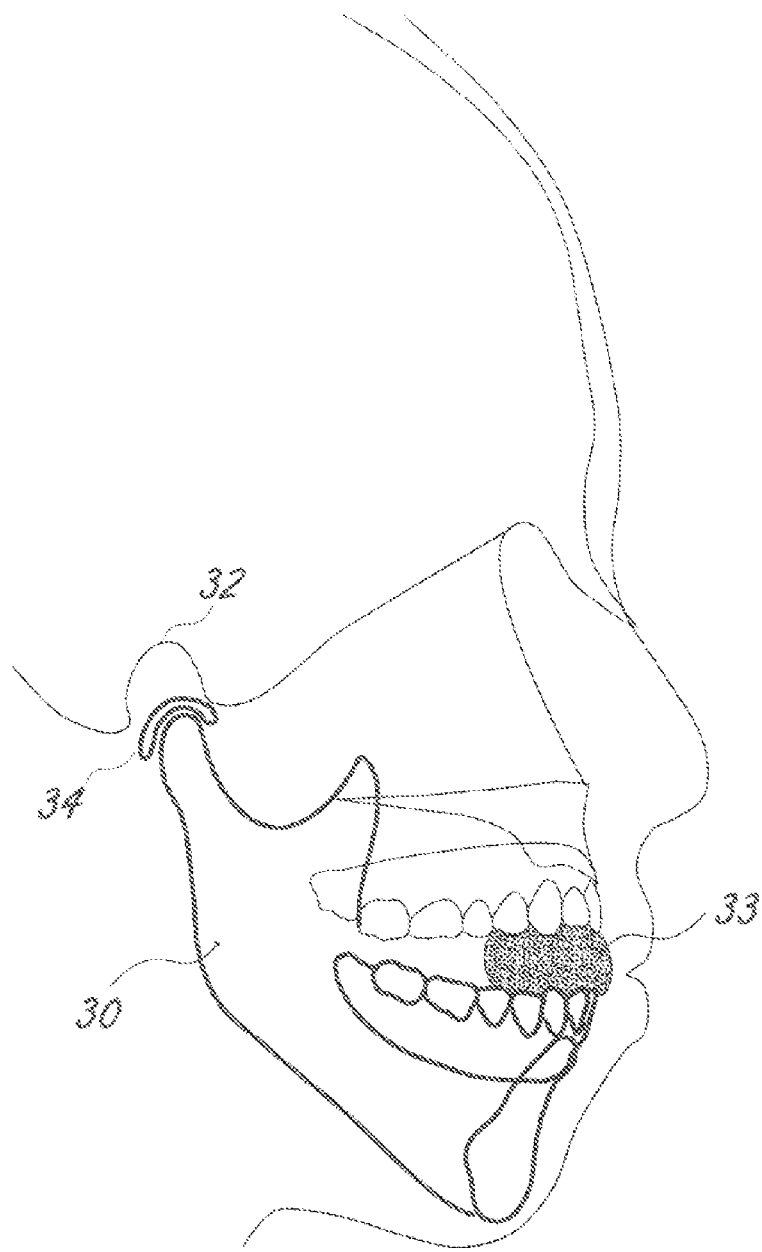
FIG. 6 shows a fusing of upper and lower jaw movements and tomography data.

FIG. 6 shows, in an exemplary manner, the soft tissue parts 34 (disk) and tracheal wall, the position and form of which cannot be established by purely applying a rigid transformation. What is also shown is the lingual bone (hyoid), which is likewise connected in a non-rigid manner to the lower jaw by means of muscles and ligaments. However, by using the scan splint 33 according to the present invention, it is now possible to generate a (further) slice image which can image the precise position and shape of the soft tissue parts 34 or the position of the bone, which is not mounted rigidly in respect of the lower jaw.

The present invention is not limited to embodiments described herein; reference should be had to the appended claims.

What is claimed is:

1. A method for generating a virtual jaw image which comprises an arrangement of joint elements in a mandibular joint, the method comprising:
   recording a tomographic jaw image which comprises a digital lower jaw image and a digital upper jaw image so as to obtain a recorded tomographic jaw image;
   performing a movement recording method to obtain a movement record, the movement recording method comprising producing at least one position data record during a recording, wherein each of the at least one position data record describes a spatial position of a lower jaw in relation to an upper jaw at a specific time;

scanning surface sections of the upper jaw and of the lower jaw at a defined time during the movement recording method so as to obtain a spatial relation of the surface sections of the upper jaw and the lower jaw within the position data record at the defined time;

assigning at least one of the at least one position data record of a virtual position of the digital lower jaw image in relation to the digital upper jaw image set forth in the recorded tomographic jaw image to fuse the recorded tomographic jaw image with the position data record;

selecting one of the at least one position data record so as to obtain a selected position data record;

virtually aligning the digital lower jaw image in relation to the digital upper jaw image in accordance with the selected position data record so as to produce the virtual jaw image; and showing a digital volumetric lower jaw image in relation to a digital volumetric upper jaw based on the recorded tomographic jaw image, wherein, the virtually aligning corresponds to a real position of the lower jaw in relation to the upper jaw in accordance with the selected position data record.

2. The method as recited in claim 1, wherein the movement recording method is a condylography method, and the movement record is a condylogram.

3. The method as recited in claim 1, wherein the scanning of the surface sections of the upper jaw and of the lower jaw at the defined time during the movement recording method is performed via a bite registration.

4. The method as recited in claim 3, wherein the recording of the digital upper jaw images and the digital lower jaw images is performed by digitalizing a bite recognition.

5. The method as recited in claim 1, wherein the recording of the digital upper jaw image and the digital lower jaw image is produced by a tomographic imaging method in a jaw position.

6. The method as recited in claim 1, further comprising:
selecting a time in the movement record to select the selected position data record; and
identifying the selected position data record based on the time selected.

7. The method as recited in claim 1, further comprising:
selecting an element of the digital upper jaw image or an element of the digital lower jaw image; and
displaying a movement track of the element selected based on the movement record.

8. A method for producing a scan splint, the method comprising:
generating a virtual jaw image pursuant to the method as recited claim 1; and
producing the scan splint based on the virtual jaw image,
wherein, the scan splint comprises at least one defined upper jaw abutment surface and at least one defined lower jaw abutment surface, the at least one defined upper jaw abutment surface and the at least one defined lower jaw abutment surface being aligned with respect to each another so that the lower jaw assumes the spatial position in relation to the upper jaw in accordance with the selected position data record when the at least one upper jaw abutment surface abuts the upper jaw and the at least one lower jaw abutment surface abuts the lower jaw.

9. A method for producing a digital image, the method comprising:
bringing the scan splint manufactured according to the method as recited in claim 8 into abutment with the lower jaw and the upper jaw;
imaging the upper jaw and the lower jaw with the scan splint applied using a tomographic image recording method; and
producing an image with the tomographic image recording method so as to depict at least one body part in accordance with the selected position data record.

10. The method for producing a digital image as recited in claim 9, wherein the at least one body part is a jaw region.

11. The method for producing a digital image as recited in claim 9, wherein the image recording method is a tomographic image recording method.

12. A scan splint manufactured using the digital image as recited in claim 9.

* * * * *